US00PP36479P2

(12) United States Plant Patent
Delabroye

(10) Patent No.: US PP36,479 P2
(45) Date of Patent: Feb. 18, 2025

(54) ***HEUCHERA* PLANT NAMED 'Purple Rain'**

(50) Latin Name: ***Heuchera* hybrid**
Varietal Denomination: Purple Rain

(71) Applicant: Thierry Delabroye, Hantay (FR)

(72) Inventor: Thierry Delabroye, Hantay (FR)

(73) Assignee: Sandrine Delabroye, Hantay (FR)

( * ) Notice: Subject to any disclaimer, the term of this patent is extended or adjusted under 35 U.S.C. 154(b) by 0 days.

(21) Appl. No.: 18/614,721

(22) Filed: Mar. 24, 2024

(51) Int. Cl.
*A01H 5/02* (2018.01)
*A01H 6/80* (2018.01)

(52) U.S. Cl.
USPC ..... Plt./440

(58) Field of Classification Search
USPC ..... Plt./440
CPC ... A01H 5/12; A01H 5/02; A01H 5/00; A01H 6/80
See application file for complete search history.

(56) References Cited

U.S. PATENT DOCUMENTS

PP31,222 P2 * 12/2019 Hansen ..... A01H 5/02 Plt./440
PP31,224 P2 * 12/2019 Hansen ..... A01H 6/80 Plt./440

* cited by examiner

*Primary Examiner* — June Hwu
(74) *Attorney, Agent, or Firm* — Penny J. Aguirre

(57) ABSTRACT

A new cultivar of *Heuchera* plant named 'Purple Rain' that is characterized by its compact plant habit, its foliage that is velvety purple in color with black veins, its foliage with an upper leaf surface that is moderately glossy, and its evergreen foliage in U.S.D.A. Zone 7 or greater.

3 Drawing Sheets

Botanical classification: *Heuchera* hybrid.
Cultivar designation: 'Purple Rain'.

BACKGROUND OF THE INVENTION

The present invention relates to a new and distinct cultivar of *Heuchera* of hybrid origin, botanically known as *Heuchera* 'Purple Rain' and is hereinafter referred to by its cultivar name 'Purple Rain'.

'Purple Rain' was derived from a controlled breeding program conducted by the Inventor in his nursery in Hantay, France. The breeding program focused on obtaining a new cultivars of *Heuchera* with resistance in full sun and dry soil and dark purple foliage with black veins. 'Purple Rain' was selected in May of 2022 by the Inventor as a single unique plant derived from a cross made in May of 2021 between unnamed and unpatented proprietary plants from his breeding program.

Asexual propagation of the new cultivar was first accomplished under the direction of the Inventor by tissue culture using meristematic tissue in Rijswijk, The Netherlands in May of 2022. Asexual propagation of the new cultivar by meristem tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Purple Rain' as a unique cultivar of *Heuchera*.

1. 'Purple Rain' exhibits a compact plant habit.
2. 'Purple Rain' exhibits foliage that is velvety purple in color with black veins.
3. 'Purple Rain' exhibits evergreen foliage in U.S.D.A. Zone 7 or greater.
4. 'Purple Rain' exhibits foliage with an upper leaf surface that is moderately glossy.

Both of the parent plants of 'Purple Rain' differ from 'Purple Rain' in having faded purple leaves that are not as velvety in texture with veins that were less black in color. 'Purple Rain' can be most closely compared to the *Heuchera* cultivars 'Wildberry' (U.S. Plant Pat. No. 31,222) and 'Pink Panther' (U.S. Plant Pat. No. 31,224). Both are similar to 'Purple Rain' in having foliage that is velvety purple with black veins. Both differ from 'Purple Rain' in having leaf veins that are less black in color, and in being less vigorous. 'Pink Panther' also differs from 'Purple Rain' in having an upper leaf surface that is matte.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to a website listings by Visions for CNB New Plants.

BRIEF DESCRIPTION OF THE DRAWINGS

The accompanying color photographs illustrate the overall appearance and distinct characteristics of the new *Heu-*

*chera*. The photographs were taken of a plant 18 months in age as grown in a greenhouse in a 19-cm container in Hantay, France.

Figure 1:
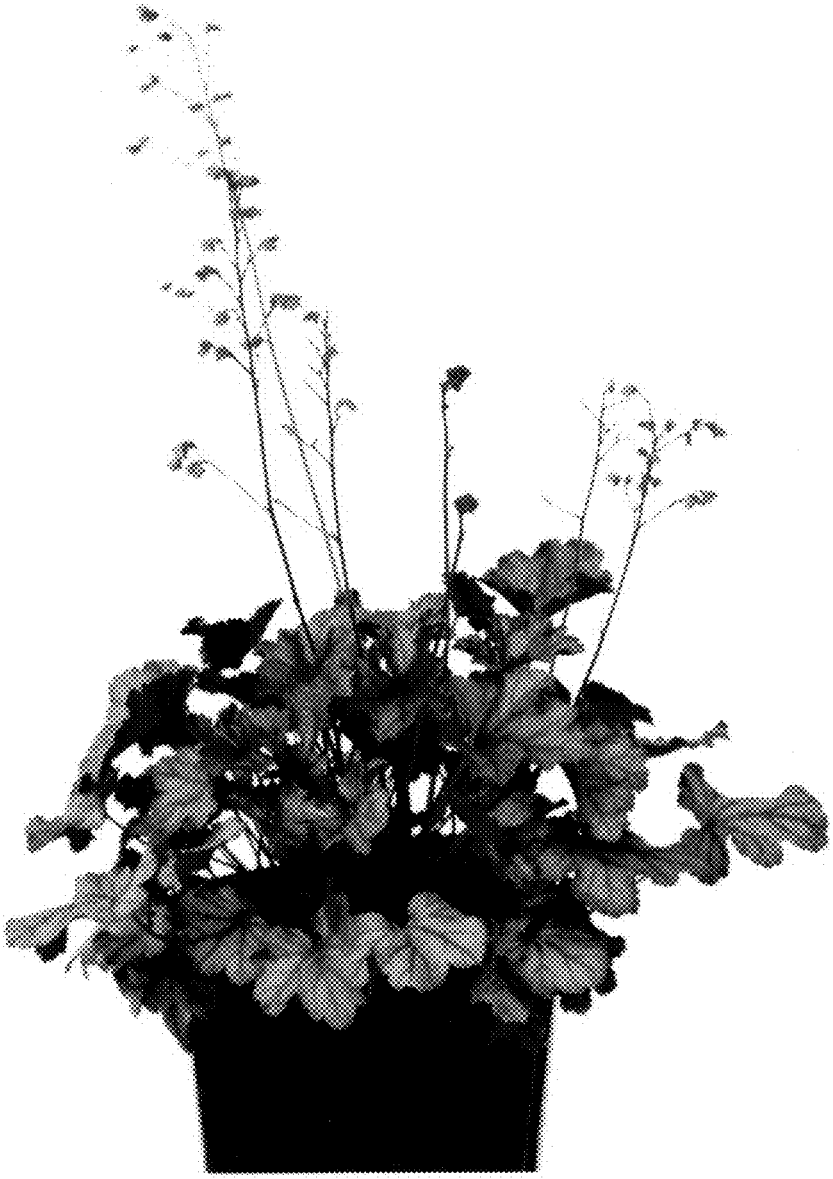

The photograph in FIG. 1 provides a side view of the plant of 'Purple Rain' in bloom.

Figure 2:
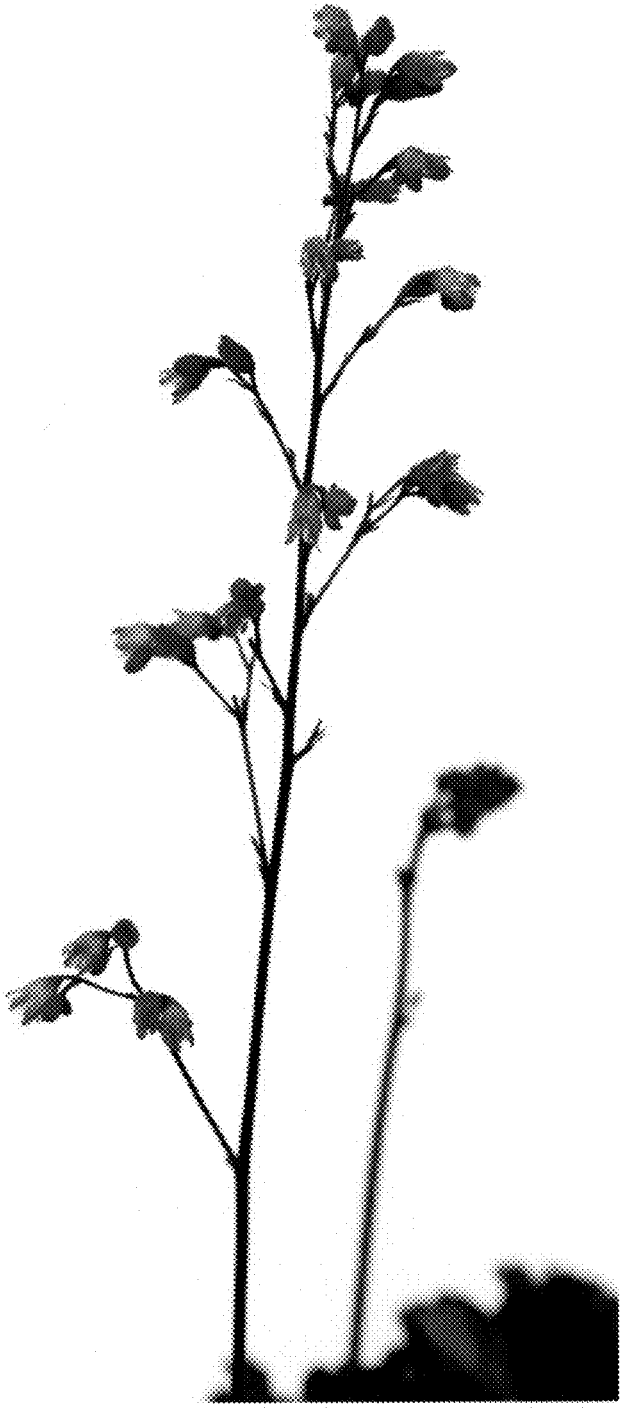

The photograph in FIG. 2 provides a close up of the inflorescence of 'Purple Rain'.

Figure 3:
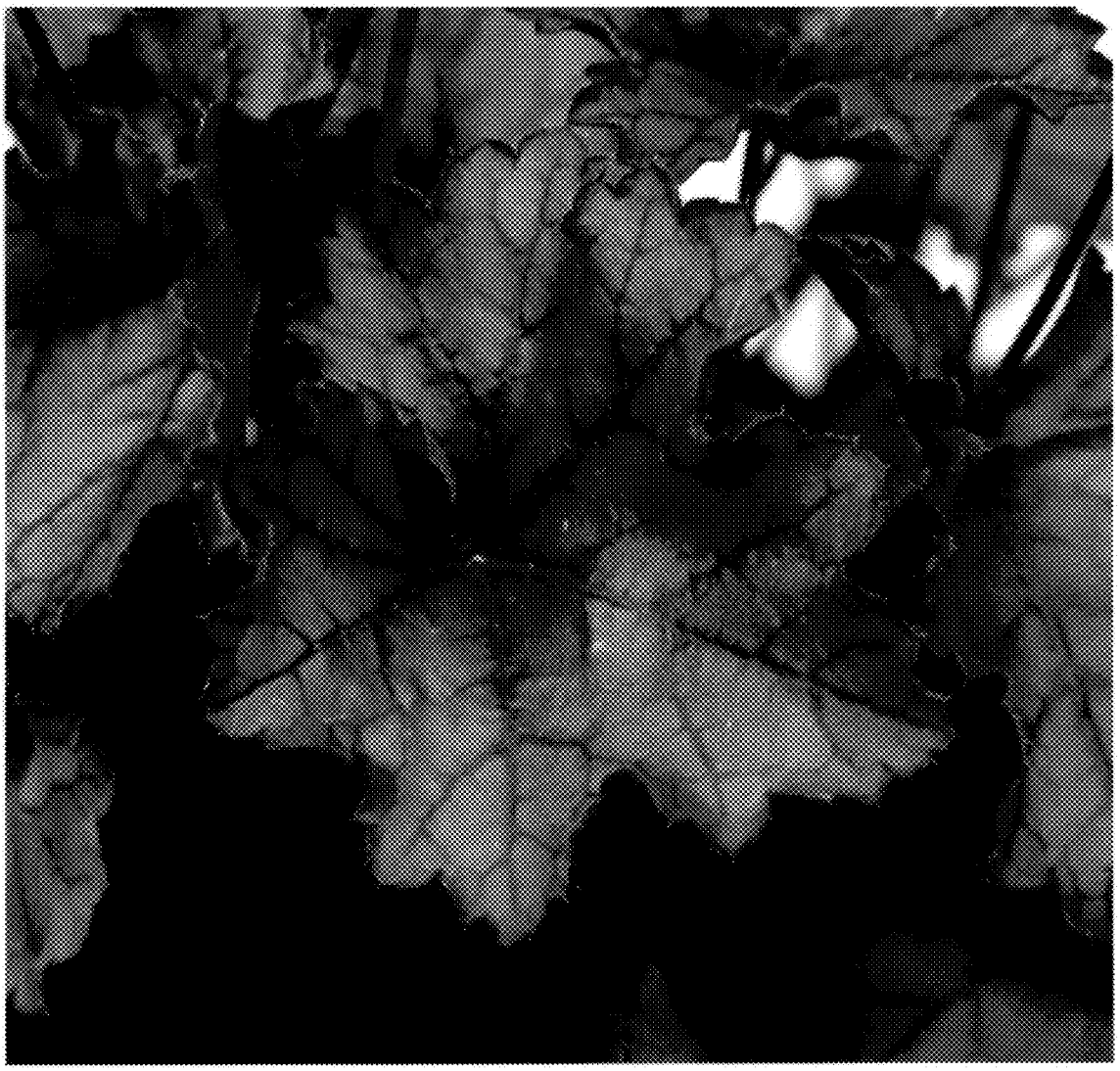

The photograph in FIG. 3 provides a close up of a young leaf of 'Purple Rain'.

The colors in the photographs are as close as possible with the photographic and printing technology utilized and the color values cited in the detailed botanical description accurately describe the colors of the new *Heuchera*.

DETAILED BOTANICAL DESCRIPTION OF THE PLANT

The following is a detailed description of 18 month-old plants of the new cultivar as grown outdoors in 19-cm containers in Hantay, France. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—May to July in The Netherlands.

*Plant type*.—Herbaceous perennial, evergreen in U.S.D.A. Zone 7 or greater.

*Plant habit*.—Compact, mounded with inflorescences held above the foliage.

*Height and spread*.—An average of 18.1 cm in height to top of foliage (42.4 cm to top of inflorescence) and 35.1 cm in width as an 18-month-old plant grown in a container.

*Hardiness*.—At least in U.S.D.A. Zones 4 to 9.

*Diseases and pests*.—Not unique susceptibility or resistance to pests or diseases has been observed.

*Root description*.—Fibrous roots on woody rootstalks, 158D in color.

*Propagation*.—Tissue culture.

*Time required for root development*.—An average of 3 weeks for root initiation in tissue culture and 6 weeks to fully develop in a plug as a young plant.

*Growth rate*.—Moderate.

Stem description (peduncle, flowering stem):

*Shape*.—Round.

*Stem color*.—N186C.

*Stem size*.—An average of 2 mm in diameter and 38.6 cm in length.

*Stem strength*.—Moderately strong.

*Stem aspect*.—Flowering stems grow at an angle of 90° to 55° (0°=horizontal).

*Stem surface*.—Moderately glossy and moderately covered with short hairs; an average of 0.5 mm in length, too small to measure color.

*Branching habit*.—Flowering stems emerge from basal rosette, average of 6 basal rosettes.

Foliage description:

*Leaf shape*.—Broadly ovate, orbicular in outline.

*Leaf division*.—Simple.

*Leaf base*.—Hastate, lobes are free to nearly touching.

*Leaf apex*.—Short abruptly acute.

*Leaf venation*.—Laciniate, upper surface 202A, lower surface a blend of N79B and N79C.

*Leaf margins*.—Crenate with abruptly acute tips on each tooth, indentations shallow and few to many in number, moderately undulate.

*Leaf attachment*.—Petiolate.

*Leaf arrangement*.—Alternate in basal rosettes.

*Leaf density*.—Medium.

*Leaf lobes*.—Lobed, an average of 7 lobes, medium in depth, divergent.

*Leaf orientation*.—Typically nearly horizontal to petiole and slightly cupped.

*Leaf surface*.—Upper surface; moderately glossy, moderately covered with very short hairs, an average of 0.2 mm in length, transparent and too small to measure color, lower surface slightly glossy, moderately covered with very short strigose hairs; an average of 0.2 mm in length, transparent and too small to measure color.

*Leaf color*.—Young upper surface; 70B, mature upper surface; a blend of N77A, N186C and 186D, young and mature lower surface; a blend of N79B and N186C, fall and winter foliage (when evergreen) is similar to mature foliage but slightly faded.

*Leaf size*.—An average of 7.2 cm in length and 6.9 cm in width.

*Leaf quantity*.—An average of 44 per plant.

*Petioles*.—An average of 13.8 cm in length and 2 mm in diameter, upper surface color; N186C, lower surface color; a blend of 187B and 187C, both surfaces are moderately glossy, moderate in strength, moderately covered with very short hairs; an average of 0.75 mm in length, transparent and NN155D in color.

*Stipules*.—Small leafy stipules at the base of each leaf, acute apex, an average of 1.1 cm in length and 4 mm in width, surface similar to leaves, N186D in color.

Flower description:

*Inflorescence type*.—Numerous small bell-shaped flowers arranged on panicles on peduncles emerging from a basal rosette.

*Inflorescence size*.—An average of 21 cm in height and 6.8 cm in diameter.

*Inflorescence number*.—An average of 7 per plant.

*Flower fragrance*.—None.

*Flower quantity*.—Average of 25 flowers per flowering stem.

*Flower Lastingness*.—Average of one week.

*Flower buds*.—Ovate in shape, an average of 0.5 mm in diameter and 0.225 mm in diameter, 58A in color, matte surface, densely covered with very short glandular hairs; an average of 0.2 mm in length and too small to measure color.

*Flower aspect*.—Upright, outwardly and nodding.

*Flower type*.—Single, campanulate.

*Flower size*.—Average of 8 mm in length and 5 mm in diameter.

*Petals*.—5, rotate arrangement and implanted in the hypanthium at base, 1 whorl, narrow elliptic in shape, margin is entire, apex is acute, base is narrow acuminate, both surfaces glabrous and smooth, an average of 3 mm in length and 1 mm in width, color; when opening upper and lower surface N66A, base 58A, when fully open upper and lower surface N66B.

*Calyx*.—Campanulate, 5 mm in length and diameter.

*Sepals*.—An average of 5, lower 70% fused into campanulate hypanthium, short oblong in shape, an average of 5 mm in length and 1 mm in width, margin is entire and fused into hypanthium, apex is obtuse, fused base, color; when opening and fully open upper surface 64B, base 64C, when opening and fully open lower surface 58A, both surfaces are matte, lower surface is densely covered with very short glandular hairs; an average of 0.2 mm in length and too small to measure color.

*Pedicels*.—An average of 1 mm in length and 0.5 mm in diameter, primary flower aspect straight on top of secondary pedicel, secondary and tertiary flower aspect is 40°, color; a blend of N186C and 200B, moderate in strength, surface matte and densely covered with very short soft glandular hairs; average of 0.2 mm in length and too small to measure color.

Reproductive organs:

*Gynoecium*.—Pistils; 2, 4.5 mm in length, stigma; club-shaped, 155A in color, 0.2 mm in diameter, style; an average of 4.25 mm in length and N155B in color, ovary; 151B in color.

*Androecium*.—Stamens; 5, anthers; ovate in shape, 0.5 mm in length and 200A in color, filament; 2 mm in length, 76C in color, pollen; low in quantity and 155A in color.

*Seed/fruit*.—No fruit or seeds were observed to date.

It is claimed:

1. A new and distinct cultivar of *Heuchera* plant named 'Purple Rain' as herein illustrated and described.

* * * * *